United States Patent [19]

Musselman

[11] 3,958,765
[45] May 25, 1976

[54] SYRINGE AND NEEDLE GRINDER

[76] Inventor: James A. Musselman, 124 N. College, Salina, Kans. 67401

[22] Filed: May 12, 1975

[21] Appl. No.: 576,704

[52] U.S. Cl. .............................................. 241/99
[51] Int. Cl.² ........................................ B02C 19/12
[58] Field of Search ............... 241/55, 99, 100, 154, 241/188, 242, 257 R, 260

[56] References Cited
UNITED STATES PATENTS

| | | | |
|---|---|---|---|
| 3,353,756 | 11/1967 | Morgenson | 241/99 |
| 3,756,520 | 9/1973 | Hughes | 241/99 |
| 3,814,332 | 6/1974 | Nakao | 241/99 |

Primary Examiner—Granville Y. Custer, Jr.
Attorney, Agent, or Firm—Edward L. Brown, Jr.

[57] ABSTRACT

A syringe and needle grinder incorporating a cylindrical-shaped rotor cutting device which is rotated within a stationary housing having an intake duct in the top of the housing offset from the center of rotation of the cutting device and a discharge duct in the bottom sidewall of the housing. The first set of cutting blades extend radially from the hub of the rotor and a second set of cutting blades are longitudinally positioned around the periphery of the rotor which act in conjunction with a plurality of stationary blades on the inside of the housing to further grind and shear the material prior to expelling it from the discharge opening.

8 Claims, 4 Drawing Figures

SYRINGE AND NEEDLE GRINDER

BACKGROUND OF THE INVENTION

Since the advent of the throwaway syringe and other medical throwaway articles there has arisen a need for a method to prevent their misuse. In hospitals today there is a tremendous volume of these articles which after being used must be accounted for by some method or another, all of which takes precious time. There is an acute need for a disposing system which is sanitary, quick to use and can handle large volumes.

The basic principle of breaking and grinding syringes by mechanical means is well known in the art as typified by U.S. Pat. No. 3,756,520. The concept of a dual-stage cylindrical cutting means as taught in the present invention is a clearly new concept in the art. The radial blades in the top surface of the rotor element extend outwardly from the hub of the rotor and comprise the first cutting means which pass by the material inlet pipe thereby breaking up the syringes as they fall into the center of the rotor element. The second stage cutting means includes a plurality of longitudinal blades positioned around the periphery of the cylindrical rotor element in conjunction with stationary blades located around the inside wall of the housing so that as the entering materials are caused to rotate by the rotating element, they are thrown outward by centrifugal force and sheared between the stationary and longitudinal blades thereby further breaking up the material.

It is therefore the principal object of the present invention to provide a new and improved syringe disposal system.

Another object of the present invention is to provide a disposal system which handles a relatively large volume of material in a very short period of time. Another object of the present invention is to provide a disposal system which would be completely sanitary and self-contained.

Figure 1:
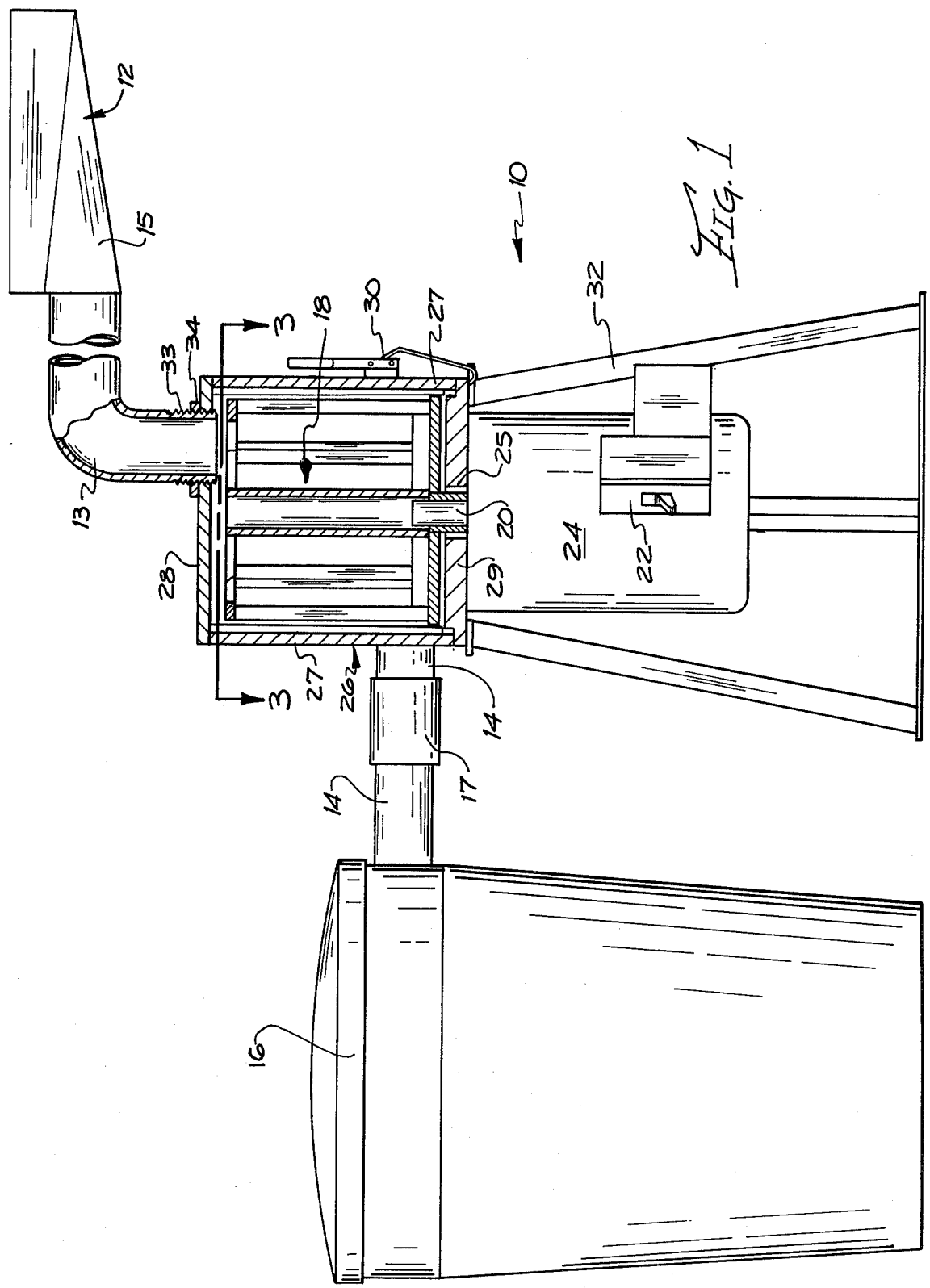
FIG. 1 is a planned view of the syringe and needle grinder with its accompanying discharge tank and inlet chute.

In describing the invention, particular attention is called to FIG. 1 wherein the syringe and needle grinder is generally identified by reference numeral 10. The grinder 10 is supplied with crushable articles through intake duct 13 and chute 12. The open top chute 12 has a sloping bottom 15 so that once the chute is filled, the articles are automatically fed through the grinder 10 until the chute is empty. The material is discharged from the grinder by discharge duct 14 which transmits the cut and ground articles into a vented closed top holding tank 16. Tank 16 is periodically emptied when necessary. The grinder 10 includes a cylindrical-shaped rotor element 18 rotatably mounted within a cylindrical housing 26. The rotor 18 is driven by shaft 20 of electric motor 24 through switch 22. The rotor element 18 is rotatably mounted in a single sleeve bearing 25 in the bottom of cylindrical housing 26. Housing 26 is made up of a cylindrical wall 27, a planar top plate 28 and a planar bottom plate 29. While the top plate 28 and the wall 27 are of a unitary construction, the cylindrical wall 27 is removably held on bottom plate 29 by a plurality of releasable toggle clamps 30 so as to allow ready inspection. The grinder 10 is mountably supported on an angle iron tripod stand 32. The intake pipe 13 has an adjustable sleeve 33 which is screw-threaded into top plate 28 so that the space between the end of the sleeve 33 and the rotor element 18 can be varied to adjust the size of the cut-up material. The sleeve 33 is locked in place by lock nut 34.

Figure 2:
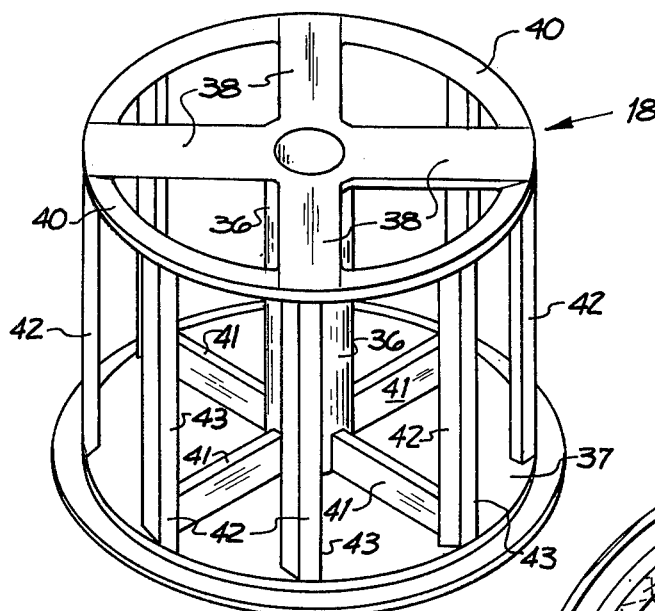
FIG. 2 is a prospective view of the rotor element removed from the housing.
Figure 3:
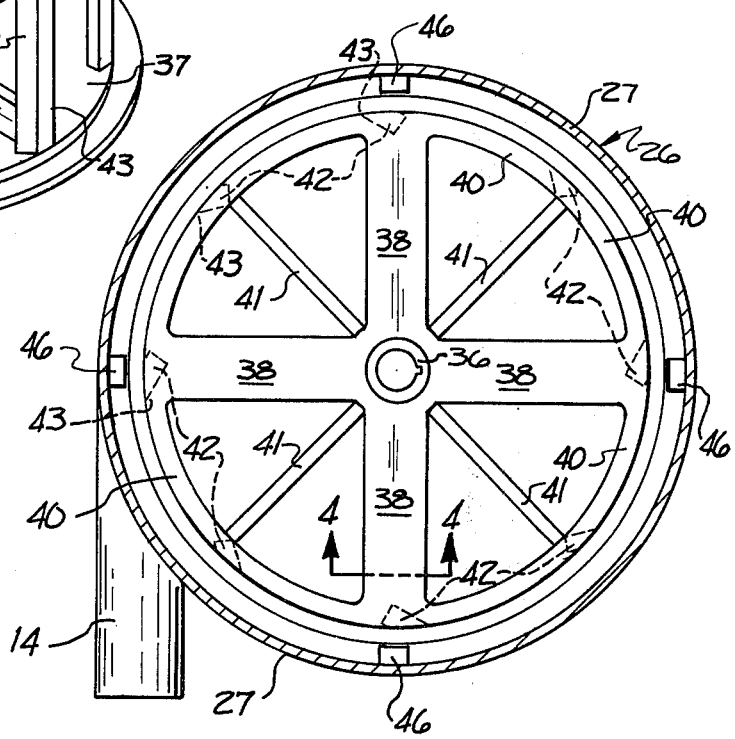
FIG. 3 is a sectional view taken along lines 3—3 of FIG. 1.
Figure 4:
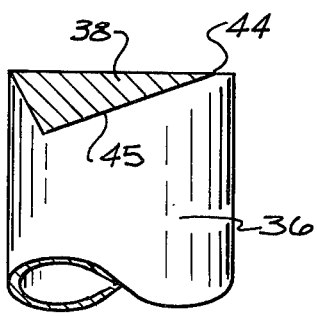
FIG. 4 is an enlarged sectional view taken along lines 4—4 of FIG. 3.

In referring specifically to FIG. 2, the rotor element 18 is basically cylindrical in shape, having a center hub 36 extending upwardly from a planar bottom plate 37 to a planar top made up of four radially spaced cutting blades 38 extending outwardly from the center hub 36 to a circular frame 40. A plurality of eight longitudinal blades 42 are located in a cylindrical pattern around the perimeter of the rotor with their upper ends attached to the circular frame 40 and their bottom ends attached to bottom plate 37. The longitudinal blades 42 have a tapered cross section to a cutting edge 43 with the plate extending inwardly from the edge 43 toward the center hub 36 and away from the direction of rotation of the rotor. A radial cutting blade 38 is shown in cross section at FIG. 4 with a cutting edge 44 and a tapered under surface 45. When blades 38 are rotated in a counterclockwise direction, the angled surface 45 forces the contacting air downwardly thereby forcing air out the discharge pipe 14 and conversely creating suction in intake 13. The radial cutting blades 38 thereby have a dual function, in first being a cutting means and secondly, a fan for sucking air through the grinder unit 10. By reason of the air passing through the grinder, the small pieces of cut and ground materials do not collect in the unit but rather are blown out the discharge pipe 14. Sleeve 17 on pipe 14 provides a joint so that tank 16 can be removed from the grinder 10. Attached to bottom plate 37 are a plurality of upwardly extending ribs 41 which extend radially outward from hub 36 to join with blades 42. When rotor 18 is in motion, the various broken syringe parts fall to the bottom of the rotor where they are engaged by ribs 41 and centrifugally thrown outward. Anchored to the inside surface of housing wall 27 are four longitudinally extending bar members 46 which are quadrangularly spaced around the inside of housing 26. The radial spacing between bars 46 and the longitudinal blades 42 is quite substantial since it is not necessary to grind up the articles into very small pieces.

OPERATION

When motor 24 is turned on, the rotor 18 will rotate at a speed in the vicinity of 3400 to 3450 r.p.m. Due to the angled surface 45 of blades 38 and the centrifugal effect upon the air by the blades, the rotor 18 functions as a blower creating suction in the intake pipe 13 and positive air pressure at the discharge pipe 14. The suction in pipe 13 draws the syringe and other articles in the chute 12 down into the grinder housing 26. As the syringes pass from the end of sleeve 33 they are initially cut by the shearing action of rotating blades 38.

As the sheared material falls to the bottom 37 of rotor 18, it comes in contact with the rotating ribs 41 which in turn throw the material centrifugally outward into the second cutting means of the rotor. The second cutting means of the rotor includes the moving blades 42 on the rotor and the stationary blades 46 on the inside of the housing 26. As the materials pass between the blades there is a second shearing action which further breaks up the materials. A wide tolerance between the blades allows the material to pass at a comparable size, since it is not necessary to fine grind the material. The ground material now at the bottom of the housing 26 is forced by centrifugal action and air out the discharge pipe 14 into the vented storage container 16. Due to the sucking action created by the rotor 18, the grinder 10 is completely emptied of materials without the necessity of periodic cleaning.

If it is desired to change the particle size of the ground material, the locking nut 34 can be released and sleeve 33 moved to a closer position with respect to cutting blades 38.

The drawings and description relate only to a preferred embodiment of the invention. Since many changes can be made in the structure of this embodiment without departing from the inventive concept, the following claims should provide the sole measure of the scope of the invention.

Having described the invention with sufficient clarity to enable those familiar with the art to construct and use it, I claim:

1. A material grinding device utilized to break up syringes, bottles and other hospital disposable items comprising:
   a cylindrical housing havng a cylinder wall, planar top and bottom end plates;
   a cylindrical-shaped rotor element rotatably positioned within the housing;
   power means to drive the rotor element;
   a material intake pipe in the top end plate of the housing offset from the center of the housing;
   a material discharge pipe in the wall of the housing;
   the rotor element including a first cutting means in the form of a plurality of radial blades radiating outwardly from the axis of rotation of the rotor element in proximity with the end of the material inlet pipe whereby material entering the housing is initially cut by the first cutting means;
   second cutting means in the rotor element in the form of a plurality of longitudinal blades positioned around the periphery thereof in parallel spaced relation to the axis of rotation of the rotor and stationary blades positioned around the inside of the wall of the cylindrical housing in parallel spaced relation with the longitudinal blades of the rotor element whereby rotation of the rotor element centrifugally discharges the ground material through the outlet pipe.

2. A material grinding device as set forth in claim 1, wherein the material inlet pipe includes an adjustable end portion where the distance between the end of the inlet pipe and the first cutting means can be adjusted to vary the size of the discharged ground material.

3. A material grinding device as set forth in claim 1, wherein the rotor element has a center hub extending through a planar bottom, the radial cutting blades extending outwardly from the center hub to a circular frame and together forming said top of the rotor, the longitudinal blades being located in a cylindrical pattern with their upper ends attached to the circular frame and their bottom ends to the planar bottom.

4. A material grinding device as set forth in claim 1, wherein the rotor element has a center hub extending through a planar top and planar bottom, the radial cutting blades extending outwardly from the center hub to a circular frame and together forming said top of the rotor, the longitudinal blades being located in a cylindrical pattern with their upper ends attached to the circular frame and their bottom ends to the planar bottom; a plurality of upwardly extending ribs attached to said bottom of the rotor extending radially outward from the hub whereby any material contacted by the ribs is thrown centrifugally outward into the second cutting means.

5. A material grinding device as set forth in claim 1, wherein the rotor element is cylindrical in shape having a center hub extending through a planar top and planar bottom, the radial cutting blades extending outwardly from the center hub to a circular frame and together forming said top of the rotor, the longitudinal blades being located in a cylindrical pattern with their upper ends attached to the circular frame and their bottom ends to the planar bottom; the longitudinal blades have a tapered cross section to a cutting edge with the blade extending inwardly from the edge toward the center of the rotor and away from the direction of rotation of the rotor.

6. A material grinding device as set forth in claim 1, wherein the rotor element is cylindrical in shape having a center hub extending through a planar top and planar bottom, the radial cutting blades extending outwardly from the center hub to a circular frame and together forming said top of the rotor, the radial cutting blades having a tapered cross section to a cutting edge, the longitudinal blades being located in a cylindrical pattern with their upper ends attached to the circular frame and their bottom ends to the planar bottom.

7. A material grinding device as set forth in claim 1, including a plurality of upwardly extending ribs attached to the center of the rotor element extending radially outwardly whereby any material contacted by the ribs is thrown centrifugally outward into the second cutting means.

8. A material grinding device as set forth in claim 1, wherein the blades of the first cutting means have an angled surface which, when rotated, creates a suction at the inlet pipe and a positive pressure at the discharge pipe.

* * * * *